United States Patent [19]

Sikes et al.

[11] Patent Number: 4,603,006

[45] Date of Patent: Jul. 29, 1986

[54] INHIBITION OF INORGANIC OR BIOLOGICAL CACO₃ DEPOSITION BY SYNTHETIC POLYSACCHARIDE DERIVATIVES

[75] Inventors: C. Steven Sikes, Mobile, Ala.; A. P. Wheeler, Clemson, S.C.

[73] Assignee: University of South Alabama, Mobile, Ala.

[21] Appl. No.: 563,145

[22] Filed: Dec. 19, 1983

[51] Int. Cl.⁴ .............................................. C02F 5/10
[52] U.S. Cl. .................................. 252/180; 252/175; 210/698; 427/384
[58] Field of Search ................... 210/698; 134/22.14; 252/89.1, 82, 86, 87, 174.17, 174.24, 180, 181, DIG. 2, DIG. 11; 427/384

[56] References Cited

U.S. PATENT DOCUMENTS

| | | | |
|---|---|---|---|
| 2,678,303 | 5/1954 | Bonewitz et al. | 252/156 |
| 3,188,289 | 6/1965 | Kahler et al. | 210/698 |
| 3,541,009 | 11/1970 | Arendt et al. | 252/180 |
| 3,791,978 | 2/1974 | Krueger et al. | 252/180 |
| 4,061,585 | 12/1977 | Finn et al. | 252/174.17 |
| 4,087,371 | 5/1978 | Lowicki et al. | 252/180 |

OTHER PUBLICATIONS

J. Biochem. 99 (1979), "Biocalcification by the Marine Alga . . . " De Jong et al, pp. 559-567.
Sigma Chemical Co. Price List, 2/1984, p. 753.
Methods in Enzymology, vol. L, Part C (1978), "Chemical Synthesis of Oligosaccharides", Flowers, pp. 93-121.
Biomin. and Biol. Metal Accumulation (1983), "Calcification in Coccolithophorids", De Jong et al, pp. 291-301.
Biomin. and Biol. Metal Accumulation (1983), "Inhibition of CaCO₃ Precipitation . . . ", Borman et al, pp. 303-305, Jan. 1983.
"Aspects of Calcification in Emiliania . . . ", De Jong et al, pp. 135-153.
J. Biochem. 129 (1982), "The Role in CaCO₃ Crystallization . . . " Borman et al, pp. 179-183.
J. Biochem. 70 (1976), "Isolation and Characterization of a Ca²⁺-Binding . . . ", De Jong et al, pp. 611-621.
Biomin. and Biol. Metal Accumulation (1983), "A Systematic Approach to Some Fundamental . . . " Sikes et al, pp. 285-289.
"Preparation of High Polymers . . . ", (7/1966), Ruckel et al, pp. 2233-2239.
"Steric Control in the Polymerization of . . . ", (8/1968), Zachoval et al, pp. 1165-1169, J. of Am. Chem. Soc. 91:5.
Monsanto, Technical Bulletin No. IC/SCS-3: 1-35, Dequest 2010 Phosphonate for Scale and Corrosion Control, Chelation, Dispersion.
Hall and Khorana, Syntheses of Pyrimidine Nucleoside-2'(3'),5'-Diphosphates, (Contribution from the Chemistry Div. of British Columbia Research Council), (Apr. 5, 1955):1871.
Mary Feiser, in Fieser and Fieser's, vol. 8: 146 (1980), Reagents for Organic Synthesis.
Feiser L. F. and Fieser M., vol. 1: 904 and 1127-1128 (1967), Reagents for Organic Synthesis.

*Primary Examiner*—Prince E. Willis
*Attorney, Agent, or Firm*—Oblon, Fisher, Spivak, McClelland & Maier

[57] ABSTRACT

The present invention relates to a method of inhibiting the formation of calcium carbonate-containing deposits on a surface by applying a composition comprising an anticalcification-effective amount of a polysaccharide or derivative thereof. The present method is useful for the prevention and/or retardation (inhibition) of inorganic scaling, as well as, for the inhibition of fouling by plant or animal organisms.

17 Claims, No Drawings

INHIBITION OF INORGANIC OR BIOLOGICAL CACO₃ DEPOSITION BY SYNTHETIC POLYSACCHARIDE DERIVATIVES

Work for the present invention was supported in part by a grant from the U.S. Department of Commerce, National Oceanic and Atmospheric Administration.

BACKGROUND OF THE INVENTION

1. Field of the Invention

This invention relates generally to the subject matter of inorganic and biological CaCO₃ formation. More particularly, it relates to the inhibition of CaCO₃-containing deposits by synthetic polysaccharide derivatives. These derivatives have been found effective for the inhibition of the formation of inorganic or biological CaCO₃-containing deposits on a surface with which they are contacted.

2. Description of the Prior Art:

Control of CaCO₃-encrustation and growth of calcifying organisms on surfaces in marine environments has long been recognized as a potentially solvable problem. By preventing or slowing the occurrence of these "fouling" substances in organisms, the useful lifetime of surfaces such as hulls of ships and pilings of docks can be increased. In the case of hulls of ships, prevention of fouling also has the effect of allowing the ship to move more efficiently through the water.

Historically, the problem has been approached by impregnating or coating surface with compounds that interfere with the metabolism of fouling organisms. For example, the use of inhibitors of carbonic anhydrase, an enzyme often involved in calcification, has been suggested for such use (Costlow, J. D., Physiol. Zoology 32:177 (1959). More recently, inhibitors of the enzyme polyphenol oxidase, also involved in the calcification process have been shown effective as anti-fouling compounds (Turner, R. D., Symposium on Marine Biodeterioration, Naval Institute Press, Washington, D.C.). Less specific metabolic inhibitors, such as organotin compounds, are also being applied (Good, M. L., Symposium on Marine Biodeteroration, supra).

In addition, CaCO₃ crystal growth occurs abiotically in most natural solutions leading to unwanted calcified deposits. For example, scale builds up anywhere in the sea where nucleation occurs, because sea water is supersaturated with respect to CaCO₃ by a factor of 5 to 10-fold, allowing crystal growth to proceed spontaneously (Stumm, W., and Morgan, J. J., Aquatic Chemistry, John Wiley and Sons, Somerset, N.J. (1981)). Inorganic scales are also often encountered as unwanted deposits in pipes and boilers where supersaturation becomes a problem due to evaporative concentrations of ions. Carboxylates, such as NTA, ethylene diamine tetraacetate (EDTA) and gluconates have been used to retard or inhibit the precipitation of supersaturated solutions of calcium carbonate, although somewhat high concentrations are needed for these compounds to act as effective inhibitors. Hexametaphosphate, at 1–10 ppm concentration was found to retard scaling leading to the widespread use of polyphosphates as scale inhibitors in municipal and industrial water systems. (Monsanto's Technical Bulletin No. IC/SCS-323, Dequest 2010 Phosphonate).

In recirculating cooling water systems, calcium carbonate is generally the predominant scalant. Since cooling towers are efficient air scrubbers, this circulating water is saturated with CO₂, establishing an equilibrium between bicarbonate and carbonate in solution. As the pH of the water rises, this equilibrium shifts towards carbonate. Heating also produces a shift in the dissolved inorganic carbon equilibrium to the right, producing calcium carbonate:

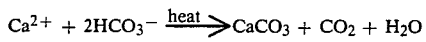

$$Ca^{2+} + 2HCO_3^- \xrightarrow{heat} CaCO_3 + CO_2 + H_2O$$

Finally, calcium carbonate shows an inverse solubility trend, being less soluble at higher temperatures. All of these factors tend to produce scaling on critical heat-transfer surfaces which reduces the heat transfer efficiency, increases frequency of required cleaning and decreases the life of the system. Several of the inhibitors of the precipitation of calcium carbonate show the phonomenon of a threshold effect, e.g., the prevention of precipitation from supersaturated solutions of scalants by substoichiometric levels of inhibitors. Present mechanistic theories postulate that the threshold agent is absorbed on the growth sites of the scalant crystallite during the process of crystallization and alters the growth pattern so that the resultant scalant crystals are formed more slowly and are highly distorted. (Reddy M. M., and Nancollas, G. H., Desalination 12:61 (1973)).

A speculative model of organic matrix structure and function, based primarily on aspects of mollusk shell proteinaceous matrix biochemistry, as well as a brief review of the proteinaceous organic matrices from various other phyla was presented by Weiner, S., Traub, W., and Lowenstam, H. A., "Organic Matrix in Calcified Exoskeltons", in Biomineralization and Biological Metal Accum., pp. 205–224 (1983), Westbroek and De Jong, Eds., Reidel Publishing Co., incorporated herein by reference. Further characterization of the various matrical components, such as the soluble matrical fraction containing glycoprotein components can be found in Krampitz, G., Drolshagen, H., Hausle, J., and Hof-Irmscher, K, "Organic Matrices of Mollusk Shell", in Biomineral. and Biol. Metal Accum., supra, pp. 231–247 (1983), incorporated herein by reference. Calciumbinding, sulfated, high molecular weight glycoproteins have been identified in the soluble matrix of several species. In addition, this soluble fraction may also contain a number of smaller molecular weight glycoprotein components (Weiner, S., Lowenstam, H. A., and Hood, L. J., J. Exp. Mar. Biol. Ecol., 30:45–51 (1977)). A further characterization of the amino acid sequence of soluble mollusk shell protein by peptide analysis afrer cleavage of the proteins on both sides of the Asp residues, showed a pattern of repeating sequence of aspartic acids separated by either glycine or serine in an alternative manner with Asp. The repeating sequence observed is of the form (Asp-Y)$_n$-type, where Y is a single amino acid. The natural proteinaceous matrix of almost all mineralized tissues studied to date (both vertebrates and invertebrates) contain proteins which are enriched in aspartic acid (Asp) and/or glutamic acid (Glu) (Veis, A., and Perry A., Biochemistry 6:2049 (1967)); Shuttlewroeth, A., and Yeis, A., Biochem. Biophys. Acta, 257:414 (1972)).

The (Asp-Y)$_n$-type sequence was hypothesized to be present in the organic matrices from a variety of molluscan species, such as *Crassostrea virginicia, Mercanaria mercenaria,. Crassostrea irredescens* and *Nautilus pompilius*, and it was suggested that these sequences played a function as a template for mineralization, although X-ray diffraction studies showed that there was a poor march between the Ca-Ca distances in the crystal lattice and the potential calcium-binding sites along the polypetide chain for this sequence (Weiner S., and Hood L., *Science* 19: 987 (1975); Weiner S., in *The Chem. and Biol. of Mineral. Connective Tissues,* Veis A., ed., pp. 517–521, Elsevier North Holland, Inc. (1981); and Weiner S., and Traub W., in *Struct. Asp. of Recog. and Assembly in Biol. Mascromolec.* Balaban, N., Sussman, J. L., Traub, W., and Yonath, A., eds., pp. 467–482 (1981), incorporated herein by reference).

Acknowledging that the process of $CaCO_3$ nucleation and crystal growth itself is central to the process of encrustation by all calcifying organisms, such as barnacles, oysters, ship worms, algae and the like, Wheeler, A. P., George, J. W. and Evans, C. A., *Science* 212: 1397 (1981), incorporated herein by reference, made the discovery that a 170,000 MW glycoprotein obtained from the proteinaceous matrix that permeates the $CaCO_3$ of oyster shell is a very potent inhibitor, rather than an initiator of $CaCO_3$ nucleation and crystal growth as previously thought. The 170,000 MW glycoprotein was identified by staining for carbohydrates and it was shown to contain 10.2% carbohydrate by weight. The molecuar weight and carbohydrate content reported for the glycoprotein form oyster shell are comparable to those observed for the protein obtained from clams by Crenshaw, M. A., *Biomineralization* 6: 6 (1972), incorporated herein by reference.

Wheeler, A. P., and Sikes, C. S., in concurrently filed and copending application entitled "Inhibition of the Formation of Inorganic or Biological $CaCO_3$-Containing Deposits by a Proteinaceous Fraction Obtained From $CaCO_3$-Forming Organisms", incorporated herein by reference, disclose a method of inhibiting the formation of $CaCO_3$-containing deposits with a glycoprotein-containing fraction isolated from $CaCO_3$-containing tissues obtained from $CaCO_3$-forming plants or animals. As such, the glycopeptide-like materials have been shown to have a broad range of MW ranging from 400 to $10^8$, and higher.

Sikes, C. S. and Wheeler, A. P., in concurrently filed and copending application entitled "Inhibition of Inorganic or Biological $CaCO_3$ Deposition by Poly Amino Acid Derivatives", incorporated herein by reference, further disclose a method of inhibiting the formation of inorganic or biological $CaCO_3$ deposition by applying a synthetic amino acid polymer having a proteinaceous matrix-like structure.

Coccolithophoridae are calcareous algae characterized by their ability to form a calcified cell cover consisting of calcite plates called coccoliths. The coccoliths from the species *Emiliania huxleyi* were shown to contain a water-soluble acid polysaccharide possessing $Ca^{+2}$-binding capacity (de Jong, E. W., Bosch L. and Westbroek, P., *Eur. J. Biochem.*, 70:611–621 (1976)). The polysaccharides were characterized to have a heterogeneous matrix containing uronic acid and having high affinity and low affinity sites for binding of $Ca^{+2}$. (de Jong, E. W., Dam, W., Westbroek, P., and Crenshaw, M. A., in The Mech. of Mineral. in the Invertebrates and Plants, Watabe, N., and Wilbur, K. M., eds., University of S. Carolina Press, Columbia, S.C. pp. 135–153 (1976), incorporated herein by reference). The polysaccharide matrix was also shown to contain ester sulphates by incorporation of radioactive sulphated groups (de Jong, E., Van Rens, L., Westbroek, P. and Bosch, L., *Eur. J. Biochem.* 99:559–567 (1979), incorporated herein by reference).

Sikes, C. S., and Wheeler, A. P., in concurrently filed and co-pending application entitled "Inhibition of Inorganic and Biological $CaCO_3$ Deposition by a Polysaccharide Fraction Obtained from $CaCO_3$-forming Organisms" incorporated herein by reference, disclose a method of inhibiting the formation of $CaCO_3$-containing deposits by applying a polysaccharide-containing fraction, substantially free of protein components, isolated from $CaCO_3$-containing tissues obtained from $CaCO_3$-forming plants or animals. As such, the polysaccharide-containing materials have been shown to have a broad range of MW ranging from 500 to $10^8$, and higher.

None of the cofiled, copending applications by the present inventors are considered prior art to the present invention.

An interest in further elucidating the role played by the structural part of the polysaccharide matrix from $CaCO_3$-forming animals in the inhibition of $CaCO_3$ encrustation and growth of calcifying organisms, prompted the present inventors to search for other potent and commercially useful inhibitors of said processes. This successful innovation and perfection, for the first time, of obtaining synthetic biopolymers having a natural polysaccharide matrix-like structure, resulting in a significant number of novel and highly potent calcium carbonate-position inhibitors, now opens the possibility of using the synthetically derived biopolymers for the inhibition of calcium carbonate deposition in pipes, boilers and the like, of widespread use and indusrrial environments, as well as for the prevention of fouling of surfaces in marine environments. The use of these highly potent inhibitors for the inhibition or retardation of calcium carbonate deposition has heretofore been unknown in the art.

SUMMARY OF THE INVENTION

The present invention relates to a method of inhibiting the formation of $CaCO_3$-containing deposits on a surface by applying a composition comprising an anticalcification-effective amount of a polysaccharide derivative. The present method is useful for the prevention and/or retardation of inorganic scaling, as well as, for the inhibition of fouling by plant or animal organisms.

A more complete appreciation of the invention and many of the attendant advantages thereof, will be readily perceived as the same becomes better understood by reference to the following detailed description of the present invention.

DETAILED DESCRIPTION OF THE INVENTION

The present invention arose from the analysis of the monosaccharide composition of matrices of calcified structures from calcareous algae, and the like. The potential role of negatively charged sulfated, phosphated or carboxylated derivatives of sugar residues, such as galactose, mannose, glucose, and the like, as "active sites" for nucleation and crystal formation, led the present inventors to the speculation that simpler synthetic polymers carrying negatively charged monosaccharide residues at appropriate locations within a polymeric structure would interfere with the calcifying activity of the $CaCO_3$ structure-forming plants and animal organisms.

The present invention discloses a method of preventing the formation of $CaCO_3$-containing deposits on a surface comprising, applying to said surface a composition comprising an anticalcification effective amount of a polysaccharide of at least 500 MW, of the formula:

$$\text{Poly } (X_n Y_m)$$

wherein the polymer is formed by $\alpha$ or $\beta$ glycosidic linkages between adjacent monomers;

wherein each X, independently, is the radical of an L or D furanosic or pyranosic monosaccharide or disaccharide containing 5 to 7C containing at least one group of the formula:

$$-R^3 \quad -(CR_2^2)_r$$

attached through a C wherein each $R^2$, independently, may be H, $C_1$-$C_4$ alkyl, $C_1$-$C_4$ alkenyl, $C_1$-$C_4$ alkynyl, $C_1$-$C_4$ haloalkyl, $C_1$-$C_4$ haloalkenyl, $C_1$-$C_4$ haloalkynyl, halogen, OH, $C_1$-$C_4$ ether or $C_1$-$C_4$ amine;

r, may be 0-4;

each $R^3$, independently, is COOH, $CONH_2$, $COR^4$, $COOR^4$, COOM, $SO_4H$, $SO_3HNH_2$, $SO_3R^4$, $SO_4R^4$, $SO_4M$, $PO_4H_2$, $PO_3HNH_2$, $PO_4HR^4$, $PO_2H(OR^4)_2$ or $PO_4R_2^4$, wherein each $R^4$, independently, is $C_1$-$C_4$ alkyl, $C_1$-$C_4$ alkenyl, $C_1$-$C_4$ alkynyl, $C_1$-$C_4$ haloalkyl, $C_1$-$C_4$ haloalkenyl, or $C_1$-$C_4$ haloalkynyl; M is Na, K, ½ Ca or ½ Ba;

each Y, independently may be X where $R^3$ may further be H, $C_1$-$C_4$ alkyl, $C_1$-$C_4$ alkenyl, $C_1$-$C_4$ alkynyl, $C_1$-$C_4$ haloalkyl, $C_1$-$C_4$ haloalkenyl, $C_1$-$C_4$ haloalkynyl, OH, $OR^4$, $C_1$-$C_4$ amine, $C_1$-$C_4$ alkanol or phenyl; and m/n may vary from 1 to 10, in an amount effective for inhibiting the formation of $CaCO_3$-containing deposits.

The polysaccharide structures of the present invention have been shown to have an effect on the rate of precipitation of $CaCO_3$ as measured by a change in the pH of the $CaCO_3$-containing solution. As such, the present invention relates to polymers of D or L monosaccharides attached through $\alpha$ or $\beta$ —O— glycosidic bridges in the form of a linear or branched backbone. Preferred are the polymers where the —O— glycosidic bridges are formed through 1→6 or 1→4 bonds of C-atoms corresponding to different monosaccharides although bridges formed between other C-atoms are also contemplated herein. The monosaccharide polymers of this invention are those having a MW approximately 500 to $10^8$ daltons and even higher and containing the above-indicated monosaccharide residues. Polymers having a MW lower than 500 show diminished anticalcification activity. Although the upper limit for the MW of the monosaccharide polymer is only determined by the solubility of these compounds in the medium, higher MW polymers may also be used, provided that the presence of the insoluble materials does not interfere with industrial operation. One of the preferred MW ranges for the present monosaccharide polymers is 2,000-$10^7$. Also preferred are 2,000-$10^6$, 2,000-$10^5$, 2,500-20,000 4,000-8,000 and 3,500-10,000 MW.

One of the preferred embodiments of the present invention is a homopolymer having glycosidic linkages between monosaccharides carrying a substituent derived from COOH, $PO_4H_2$ or $SO_4H$ $\alpha$ or $\beta$ and/or derivatives thereof. Any D or L monosaccharide of the above type may be used for obtaining the homopolymer of this invention. Some of the preferred monosaccharides are hexoses, pentoses, deoxyhexoses and deoxypentoses carrying COOH($R^4$), $PO_4H_2(R^4)_2$ or $SO_4H(R^4)$ substituents. Some of the most preferred monosaccharide derivatives are those carrying the substituents at the 6 position. Also preferred are the monosaccharides carrying the COOH($R^4$), $PO_4H_2(R^4)_2$ or $SO_4H(R^4)$ attached to the 2 or 3 positions. Some of the most preferred monosaccharide are galacturonic acid, glucuronic acid, mannuronic acid, and the corresponding monosaccharide carrying $PO_4H_2(R^4)_2$ or $SO_4H(R^4)$ instead of the COOH substitutent.

In another form of the present invention, the monosaccharide polymers may be random $\alpha$ or $\beta$ glycosidic co-polymers of a first D or L monosaccharide derivative of the above type with at least one other monosaccharide or derivative thereof. The other monosaccharide may be any monosaccharide, including D or L monosaccharides. Preferred are arabinose, ribose, xylose, rhamnose and derivatives thereof, although other monosaccharides and derivatives thereof are also contemplated in the present invention. The ratio of the first monosaccharide derivatives to the other monosaccharides in the polymers may vary between 1:1 to 1:10. Preferred ratios are 1:2, 1:3 and 1:4, although lower ratios are also contemplated.

Another form of the present invention encompasses ordered $\alpha$ or $\beta$ glycosidic co-polymers monosaccharides of the first type or derivatives thereof, with at least one other monosaccharide or derivative thereof. The other monosaccharide or derivative thereof in the ordered co-polymers can be any monosaccharide, including but not limited to, D or L pentoses, deoxypentoses, hexoses, deoxyhexoses, or derivatives thereof. Some of the most preferred are arabinose, ribose, xylose, and rhamnose or derivatives thereof. The ratio of the first-type monosaccharide derivatives to the other monosaccharides in the polymers may vary between 1:1 to 1:10. Preferred ratios are 1:2, 1:3 and 1:4, although lower ratios are also contemplated.

Some of the preferred homo- and co-polymers are those wherein the first monosaccharide is replaced by a disaccharide or derivatives thereof. The disaccharides may be any combination of hexoses, deoxyhexoses, pentoses, deoxypentoses and derivatives thereof carrying a COOH($R^4$), $PO_4H_2(R_2^4)$ or $SO_4H(R^4)$ substituent at positions 6, 3 or 2, although other positions are also contemplated in the present invention.

The monosaccharide polymers of the present invention have been found to have scale inhibiting properties, especially for calcium carbonate scales. As such, they can be used in sea water distillation plants, cooling systems, black liquor evaporators, waste concentrators and similar equipment. In addition, the present compounds are useful for the prevention of calcified formations by organisms such as barnacles, mollusks, sea urchins, and calcareous algae, among others. The biological formation of calcium carbonate (fouling) is a complex process intimately associated with the metabolism of the organism. The forming crystals are normally insulated from the external environment by several membranous or cellular layers. These layers represent a potential barrier that could prevent an inhibitor of calcium carbonate crystal formation, particularly macromolecular ones, from reaching the site of crystal growth.

The monosaccharide polymers of the present invention appear to be good inhibitors of biological calcification and thus are effective in controlling calcification by both plants and animals. One possibility is that a small amount of the inhibitor in the solution where the plant or animal organism exists reaches the site of calcification, and once there the mechanism of inhibition may be similar to that occuring during inorganic calcium carbonate crystal formation in vitro. However, it is also possible that the inhibitors may interfere with the metabolism of the organism, thereby inhibiting calcification indirectly.

The monosaccharide polymers of the present invention are significantly stable polymeric structures, and it appears that they are not biodegraded or deactivated through catabolism. The inhibitory potencies of the various polysaccharides are preserved for up to several hours without being metabolically degraded. Further, all MW polymers are stable and maintain their calcium carbonate-forming inhibitory activity in vitro at room temperature for over 100 hours, and even longer periods of time. In addition, the polysaccharides can resist a treatment with moderate amounts of pressure (18 psi) while preserving their characteristics and activities. Moreover, the polymers of this invention possess high stability and undiminished inhibitory activity of calcium carbonate formation when kept under refrigeration for periods of up to a year and longer.

The preparation of the various monosaccharide (or disaccharide) polymer derivatives of this invention can be accomplished by a variety of known methods (Flowers, H. M., "Chemical Synthesis of Oligosaccharides", in *Methods in Enzymology*, Vol. 50, Chapter 7:93–121, Ginsburg, V., Ed., incorporated herein by reference). However, one of the preferred methods for preparing monosaccharide polymers of this invention having different kinds of sugar molecules and specific stereochemistry are those disclosed by Ruckel, E. R., and Schuerch, C., "Preparation of High Polymers from 1,6-anhydro-2,3,4-tri-0-substituted $\beta$-D-glucopyranose", J. Org. Chem. 31:2233–2238, (1966), and modifications thereof, incorporated herein by reference. The proportion of the glycosidic isomeric composition in a polysaccharide structure can be controlled by the conditions of the reaction, as disclosed by Zachoval, J., and Schuerch, C., "Steric Control in the Polymerization of 1,6-anhydro-$\beta$-D-glucopyranose Derivatives", J. Amer. Chem. Soc. 91:1165–1169 (1969) and modifications thereof, incorporated herein by reference.

The random and ordered co-polymers can be synthesized in like manner provided that the molar quantities of various monosaccharides (or dissacharides) contained in the desired polymer are taken into consideration. Thus, if a galacturonic acid-glucuronic acid-xyluronic acid polymer is to be prepared (1:1:1), equimolar amounts of the three monosaccharides (or in other cases of disaccharides) have to be incorporated as starting materials in the reaction mixture. The MW of the thus prepared polymers will vary over a desired range. The MW range can be varied by controlling the different variables involved in the polymerization reaction. Thus, temperature, time of incubation, amounts of catalysts, polymerization initiator, and the like, can be varied for obtaining specific MW polymer ranges, as is known in the art.

The thus prepared polysaccharides can be utilized as such, or they can be further purified by known methods. Some of the preferred methods for the purification of the present polysaccharides are recrystallization from appropriate solvents, gel chromatography and solvent extraction, although other methods are also contemplated in this invention.

The carbohydrate analysis may be carried out by any known method. However, one of the preferred methods is that which uses the phenol-sulfuric acid method of Dubois, M., Gilles, K. A., Hamilton, P. A., and Smith, F., Anal. Chem. 28:350–356 (1956), and modifications thereof, which is incorporated herein by reference. The phosphate content of the monosaccharide polymers may be determined by the phosphate analysis method of Marsh, B. B., Biochim. Biophys. Acta 32:351–61 (1959), and modifications thereof, incorporated herein by reference. The sulfate analysis may be carried out by the method of Antonopoulos, C.A., Acta Chem. Scand. 16:1521–22 (1962), or modifications thereof, incorporated herein by reference.

The synthetic polysaccharide inhibitors of all MW are inhibitory of the formation of calcium carbonate deposits. Included are polysaccharides having a molecular weight range of 500 to $10^8$ K daltons. Possibly, there may be an optimum molecular size for a given polymer that is the most effective inhibitor on a weight basis. This preferred size is related to the dimensions of the forming calcium carbonate crystal nucleus. From what is currently known the polysaccharides having a molecular weight of 2,000–30,000 seem to have the highest inhibitory activity of calcium carbonate crystal formation.

The various MW polymers of this invention may be utilized directly without additives or carriers for inhibiting the deposition of calcium carbonate whether of inorganic or biological origin. Alternatively, the various polymers may be utilized by adding an effective amount of the inhibitor to a liquid in contact with a surface on which the deposits may form. Such is the case of industrially useful and commercially important containers, e.g., boilers, piping, desalinators, cooling towers, and the like. The various saccharide polymers of this invention can be added to water, water-containing liquids, or other liquids in an amount as small as 0.01 ng/ml. The upper limit for the amount of the inhibitor is only given by its solubility in the liquid to which it is added. However, if the presence of insoluble residues of these polymers does not interfere with industrial operations, it may be desirable to add these inhibitors in an amount greater than that given by their solubility limit. A preferred range of the various polysaccharide derivatives for controlling inorganic calcium carbonates scaling is $10^{-4}$–$10^2$ $\mu$g/ml. Other preferred ranges are $10^{-4}$–0.1 $\mu$g/ml and 0.1–$10^2$ $\mu$g/ml of the various polymeric derivatives.

When the present inhibitors are utilized for their anti-fouling characteristics in order to prevent the encrustations of plant or animal organisms, they can be added to a liquid, such as water, water-containting liquids or other non-aqueous liquids, preferably an amount about 0.001–1,000 $\mu$g/ml, although larger amounts can also be used. Used within this range of concentrations, the present inhibitors find an application in the prevention of encrustation of organisms in, e.g., running water piping or sewage piping, among others.

The present inhibitors can also be applied directly to a surface before it becomes in contact with $CaCO_3$-containing liquids, e.g., industrial containers, marine surfaces such as those in piers, ships, and the like. The present inhibitors may be applied by themselves or in combination with other salt deposition inhibitors, anti-rust agents, or the like and/or with a carrier, directly to the exposed surface, or they may be mixed with other polymers used for the protection of said surfaces. A variety of carriers are contemplated for the application of the present inhibitors. Some of the most common carriers include aqueous and nonaqueous liquids, gels, oils, organic and inorganic solvents, compressed gases, and the like. However, any carrier may be used according to the needs. When used in high concentrations by themselves, the polysaccharide inhibitors of this invention may be highly viscous and can be easily applied to a surface. After the application of the inhibitors, an appropriate length of time may be allowed for the penetration of the inhibitor into the surface, as is the case with porous surface materials, such as wood, ceramics and the like. Thus, a large storage of the present inhibitors is created within the material and the surface may then be sealed with a polymer. Alternatively, the various MW polymers may be mixed with a carrier to form a suspension which can be applied to a surface. The present inhibitors may be applied to any type of surface which may be exposed to the formation of inorganic or biological $CaCO_3$ deposits. Some of the most common materials to which the present inhibitors may be applied are metals, woods, synthetic polymers and copolymers, glass, ceramics, and painted or otherwise coated surfaces, although other materials are also contemplated. When in contact with the $CaCO_3$- containing liquid, the inhibitors will slowly leach out from underneath the polymeric layer. The present inhibitors may further be applied in admixture with the above polymer, e.g., paints or any synthetic polymer used for the protection of surfaces. When the present inhibitors are used in admixture wirh a polymer, they can be used in a concentration of between 0.001–90% by weight, although higher or lower concentrations are also contemplated in this invention. Some of the preferred concentrations are 1–75% by weight. Other preferred concentrations are 5–25%, 25–50% and 10–40% by weight. When applied to a surface the present inhibitors may be formulated as a powder, solution, suspension, gel, oil, aerosol, paste or viscous colloid.

Having now fully described the invention, it will be apparent to one of ordinary skill in the art that many changes and modifications can be made thereto, without departing from the spirit or scope of the invention as set forth therein.

What is claimed as new and desired to be secured by Letters Patent of the United States is:

1. A method of inhibiting the formation of $CaCO_3$-containing deposits on a surface, comprising applying to said surface an anticalcifying composition, comprising: a substoichiometric amount of a monosaccharide or disaccharide polymer of at least 500 MW of the formula Poly $(X_nY_m)$ wherein the polymer is formed by glycosidic linkages between adjacent monomers;
    wherein each X independently, is the radical of a monomer selected from the group consisting of furanosic monosaccharides, pyranosic monosaccharides and disaccharides containing 5 to 12C atoms and one group of the formula:

attached to a C-atom thereof, wherein
    each $R^2$, independently is H, $C_1$-$C_4$ alkyl, $C_1$-$C_4$ alkenyl, $C_1$-$C_4$ alkynyl, $C_1$-$C_4$ haloalkyl, $C_1$-$C_4$ haloalkenyl, $C_1$-$C_4$ haloalkynyl, halogen, OH, $C_1$-$C_4$ ether of $C_1$-$C_4$ amine;
    r is 0-4;
    each $R^3$, independently, is COOH, $CONH_2$, $COR^4$, $COOR^4$, COOM, $SO_4H$, $SO_3HNH_2$, $SO_3R^4$, $SO_4M$, $PO_4H_2$, $PO_3HNH_2$, $PO_4HR^4$, $PO_2H(OR^4)_2$ or $PO_4R_2^4$; wherein each $R^4$, independently, is $C_1$-$C_4$ alkyl, $C_1$-$C_4$ alkenyl, $C_1$-$C_4$ alkynyl, $C_1$-$C_4$ haloalkyl, $C_1$-$C_4$ haloalkenyl, or $C_1$-$C_4$ haloalkynyl; and M is Na, K, ½ Ca or ½ Ba;
    each Y, independently, is X wherein $R^3$ further is H, $C_1$-$C_4$ alkyl, $C_1$-$C_4$ alkenyl, $C_1$-$C_4$ alkynyl, $C_1$-$C_4$ haloalkyl, $C_1$-$C_4$ haloalkenyl, $C_1$-$C_4$ haloalkynyl, OH, $C_1$-$C_4$ amine, $C_1$-$C_4$ alkanol or phenyl; and
    m/n varies from 1 to 10; in an amount effective for inhibiting the formation of $CaCO_3$-containing deposits.

2. The method of claim 1 wherein the polymer has a 2,000–$10^7$ MW.

3. The method of claim 2 wherein the polymer has a MW of 2,000–$10^6$.

4. The method of claim 3 wherein the polymer has a MW of 2,500–20,000.

5. The method of claim 4 wherein the polymer has a MW of 3,500–10,000.

6. The method of claim 1 wherein the surface whereto the polysaccharide is applied is made of a material selected from the group consisting of wood, glass, ceramic, metal, synthetic polymers and copolymers, and painted or otherwise coated surfaces.

7. The method of claim 1 wherein said polymer is applied in admixture with a carrier in the form of a powder, solution, suspension, gel, oil, aerosol, paste or viscous colloid.

8. The method of claim 1 wherein the $CaCO_3$-containing deposit comprises a $CaCO_3$-forming organism.

9. The method of claim 1 wherein at least $10^{-4}$ μg/ml of the polymer are added to a liquid in contact with said surface.

10. The method of claim 8 wherein 0.001%–90% by weight of the monosaccharide polymer is applied to said surface.

11. The method of claim 9 wherein about 0.001–1,000 μg/ml of the monosaccharide polymer are added to said liquid.

12. The method of claim 7 wherein the carrier is a paint.

13. The method of claim 1 wherein the polymer is formed from a monosaccharide selected from the group consisting of glucuronic acid, galacturonic acid, mannuronic acid, methyl esters thereof and mixtures thereof.

14. The method of claim 1 wherein the polymer is formed from at least one monosaccharide selected from the group consisting of glucuronic acid, galacturonic acid, mannuronic acid in combination with at least one other monosaccharide selected from the group consisting of arabinose, ribose, xylose, and rhamnose.

15. The method of claim 14 wherein the monosaccharide polymer is selected from the group consisting of polygalacturonic acid, polyglucuronic acid, polymannuronic acid, poly (mannuronic acidarabinose), poly (mannuronic acid-ribose), poly (mannuronic acid-xylose), poly (mannuronic acidrhamnose), poly (glucuronic acid-arabinose), poly (glucuronic acid-ribose), poly (glucuronic acidxylose), poly (glucuronic acid-rhamnose), poly (galacturonic acid-arabinose), poly (galacturonic acidribose), poly (galacturonic acid-xylose) and poly (galacturonic acid-rhamnose).

16. The method of claim 1 wherein the polymer is formed from at least one disaccharide formed form two monosaccharides selected from the group consisting of hexoses, deoxyhexoses, pentoses, and deoxypentoses, wherein $R^3$ is —COOH.

17. The method of claim 16 wherein at least one disaccharide is combined with at least one monosaccharide selected from the group consisting of hexoses deoxyhexoses, pentoses and deoxypentoses, wherein $R^3$ is —COOH.

* * * * *

UNITED STATES PATENT AND TRADEMARK OFFICE
CERTIFICATE OF CORRECTION

PATENT NO. : 4,603,006
DATED : JULY 29, 1986
INVENTOR(S) : SIKES ET AL

It is certified that error appears in the above-identified patent and that said Letters Patent is hereby corrected as shown below:

Column 2, line 62, change "lewroeth, A., and Yeis," to --leworth, A., and Veis,--.
Column 2, line 66, change "virginicia" to --virginica--.
Column 2, line 66, delete ".".
Column 3, line 3, delete "march" and insert --match--.
Column 3, line 27, delete "form" and insert --from--.
Column 4, line 29, delete "position" and insert --deposition--.
Column 4, line 32, delete "indusr-" and insert --indust---.
Column 5, line 15, change "$(CR_2^2)_r - R^3$" to --$(CR_2^2)_r - R^3$--
Column 6, line 12, delete "substitutent" and insert --substituent--.
Column 8, line 57, delete "water-containting" and insert --water-containing--.

UNITED STATES PATENT AND TRADEMARK OFFICE
CERTIFICATE OF CORRECTION

PATENT NO. : 4,603,006

DATED : July 29, 1986

INVENTOR(S) : C. Steven Sikes et al.

It is certified that error appears in the above-identified patent and that said Letters Patent is hereby corrected as shown below:

In Claim 16, line 2, "form" should read -- from --.

Signed and Sealed this

Seventeenth Day of March, 1987

Attest:

DONALD J. QUIGG

*Attesting Officer*    *Commissioner of Patents and Trademarks*